(12) United States Patent
Fleming et al.

(10) Patent No.: US 6,615,496 B1
(45) Date of Patent: Sep. 9, 2003

(54) MICROMACHINED CUTTING BLADE FORMED FROM {211}-ORIENTED SILICON

(75) Inventors: James G. Fleming, Albuquerque, NM (US); Jeffry J. Sniegowski, Edgewood, NM (US); Stephen Montague, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/564,246

(22) Filed: May 4, 2000

(51) Int. Cl.[7] .............................. B26B 9/00; B21K 11/00
(52) U.S. Cl. ........................................ 30/350; 76/104.1
(58) Field of Search ........................... 30/350; 76/104.1; 407/118, 119

(56) References Cited

U.S. PATENT DOCUMENTS

| | | | |
|---|---|---|---|
| 3,342,754 A | 9/1967 | Gorham | 528/396 |
| 4,534,827 A | 8/1985 | Henderson | 216/101 |
| 5,214,011 A * | 5/1993 | Breslin | 30/350 X |
| 5,222,967 A * | 6/1993 | Casebeer et al. | 30/350 X |
| 5,317,938 A | 6/1994 | de Juan, Jr. | 76/104.1 |
| 5,380,320 A | 1/1995 | Morris | 606/33 |
| 5,579,583 A | 12/1996 | Mehregany | 30/342 |
| 5,683,592 A | 11/1997 | Bartholomew | 216/24 |
| 5,713,133 A * | 2/1998 | Bhat et al. | 30/350 |
| 5,728,089 A | 3/1998 | Lal et al. | 606/1 |
| 5,792,137 A | 8/1998 | Carr et al. | 606/29 |
| 5,842,387 A | 12/1998 | Marcus et al. | 76/104.1 |
| 5,928,161 A | 7/1999 | Krulevitch et al. | 600/564 |
| 5,944,717 A | 8/1999 | Lee et al. | 606/48 |
| 5,980,518 A | 11/1999 | Carr et al. | 606/45 |

OTHER PUBLICATIONS

J.P. Sullivan, T.A. Friedmann and A.G. Baca, "Stress Relaxation and Thermal Evolution of Film Properties in Amorphous Carbon," *Journal of Electronic Materials*, vol. 26, pp. 1021–1029, Sep. 1997.

* cited by examiner

*Primary Examiner*—Charles Goodman
(74) *Attorney, Agent, or Firm*—John P. Hohimer

(57) ABSTRACT

A cutting blade is disclosed fabricated of micromachined silicon. The cutting blade utilizes a monocrystalline silicon substrate having a {211} crystalline orientation to form one or more cutting edges that are defined by the intersection of {211} crystalline planes of silicon with {111} crystalline planes of silicon. This results in a cutting blade which has a shallow cutting-edge angle θ of 19.5°. The micromachined cutting blade can be formed using an anisotropic wet etching process which substantially terminates etching upon reaching the {111} crystalline planes of silicon. This allows multiple blades to be batch fabricated on a common substrate and separated for packaging and use. The micromachined cutting blade, which can be mounted to a handle in tension and optionally coated for increased wear resistance and biocompatibility, has multiple applications including eye surgery (LASIK procedure).

10 Claims, 5 Drawing Sheets

MICROMACHINED CUTTING BLADE FORMED FROM {211}-ORIENTED SILICON

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates in general to cutting instruments, and in particular to a micromachined cutting blade formed of monocrystalline silicon having a {211} crystalline orientation, and to a method for manufacture thereof.

BACKGROUND OF THE INVENTION

Laser in-situ keratomelleusis (LASIK) is a procedure that is widely used for laser eye surgery to correct refractive errors producing nearsightedness, farsightedness or astigmatism. The use of the LASIK procedure requires a mechanical keratome to cut a thin circular flap across the cornea of a patient's eye so that an eximer laser can then be used to remove a calibrated amount of underlying tissue from the cornea to achieve a desired refractive change. The mechanical keratome as presently used comprises a stainless steel knife blade which is rapidly oscillated during use.

Metal cutting blades can have ragged or uneven cutting edges, and can form burrs extending outward from the cutting edge. Metal cutting blades can also dull during surgical use. These defects, if present on the blade's metal cutting edge, can produce incisions that are ragged and uneven and that extend beyond a desired or critical depth. This can be harmful in reducing the precision of the surgical procedure, in increasing the time required for healing after surgery, and in affecting the patient's vision correction as a result of the surgery. To limit these harmful effects, a careful microscopic inspection of the blade's cutting edge during manufacture and before use must be performed which increases the cost of the blades and results in some blades being rejected as unsuitable for surgery. What is needed is a knife blade for keratomy that has a high degree of sharpness, and which can be reliably produced at low cost. Also needed is a knife blade which maintains its sharpness during use, and is not subject to the formation of burrs.

The present invention provides a solution to this problem by providing a cutting blade (i.e. a knife blade) formed of monocrystalline silicon that can be precisely sharpened by anisotropic etching and which, in the absence of any applied coatings, is incapable of developing burrs because of its crystalline nature.

The use of monocrystalline silicon with a {100} substrate orientation for forming a knife blade is disclosed in U.S. Pat. No. 5,579,583 to Mehregany et al. Mehregany's requirement for a {100}-oriented substrate produces a blade having a cutting angle determined by the intersection of two crystalline planes, with the cutting angle being crystallography fixed at a relatively large blade angle of either 54.7° or 109.4°. These relatively large blade angles are disadvantageous for use in eye surgery since the large blade angles would effectively reduce the sharpness of the blade and would also make it difficult for the delicate cornea flap to easily slide across the blade during cutting.

The use of monocrystalline silicon for forming various types of knife blades is also disclosed in U.S. Pat. No. 5,842,387 to Marcus et al; U.S. Pat. No. 5,928,161 to Krulevitch et al; and U.S. Pat. No. 5,980,518 to Carr et al. None of these references disclose the use of a {211} substrate orientation for forming a knife blade as used according to the present invention. Additionally, none of these references disclose a cutting edge formed in monocrystalline silicon by a pair of substantially planar cutting-edge surfaces aligned along crystalline planes of silicon and intersecting at an angle of less than 30 degrees.

An advantage of the present invention is that a cutting blade can be fabricated that is substantially free from any burrs or ragged cutting edges.

Another advantage of the present invention is that a cutting blade can be formed with a shallow cutting-edge angle of less than 30 degrees, and preferably less than 20 degrees.

A further advantage of the present invention is that the cutting edge of the blade can be coated with a deposited material such as silicon nitride, titanium nitride, tungsten, amorphous diamond or parylene for improved wear resistance, reduced friction or biocompatibility.

Yet another advantage of the present invention is that a plurality of cutting blades can be formed on a single silicon substrate (i.e. a wafer) in a batch fabrication process and then be individually separated.

Still another advantage of the present invention is that single-edged and double-edged cutting blades can be formed according to the present invention.

These and other advantages of the method of the present invention will become evident to those skilled in the art.

SUMMARY OF THE INVENTION

The present invention relates to a micromachined cutting blade that comprises an elongate body of monocrystalline silicon having a pair of substantially parallel major body surfaces, with each major body surface being aligned substantially coplanar with a {211} crystalline plane of silicon, and a substantially planar cutting edge formed in the monocrystalline silicon body at an angle to one of the major body surfaces and oriented along the length of the body. The cutting-edge angle is preferably 19.5 degrees and corresponds to the intersection of a {211} crystalline plane of silicon with a {111} crystalline plane of silicon. The cutting edge is formed by anisotropically etching the monocrystalline silicon body, with the etching terminating at a {111} crystalline plane of silicon. In some embodiments of the present invention, the cutting edge of the blade can be hardened for increased wear resistance by forming a coating of a hard material over at least a part of the cutting edge. The coating can comprise silicon nitride, titanium nitride, tungsten, or amorphous diamond. Alternately, a conformal parylene coating can be formed over a portion or the entirety of the cutting blade. The cutting blade can also include a handle connected to opposite ends of the crystalline silicon body to support the body in tension, thereby keeping the cutting edge planar. Such a handle can be, for example, U-shaped.

The present invention further relates to a micromachined cutting blade that comprises an elongate body of monocrystalline silicon having a pair of substantially parallel major body surfaces, and at least one cutting edge formed in the monocrystalline silicon body, with each cutting edge further comprising a pair of cutting-edge surfaces aligned along crystalline planes of silicon and intersecting at an angle of generally less than 30 degrees, and preferably less than 20 degrees. One of the surfaces of each cutting edge is aligned substantially coplanar with one of the body surfaces which, in turn, is substantially coplanar with a {211} crystalline plane of silicon. The other surface of each cutting edge is aligned substantially along a {111} crystalline plane of silicon. A coating of a hard material (e.g. silicon nitride, titanium nitride, tungsten, or amorphous diamond) can be provided to cover at least a part of one cutting edge of the blade to increase its wear resistance. Alternately, a conformal parylene coating can be formed over at least a portion of the cutting blade.

The present invention also relates to a method for forming a micromachined cutting blade, comprising steps for providing a monocrystalline silicon body having a pair of substantially parallel major body surfaces, with each major body surface being aligned substantially along a {211} crystalline plane of silicon; and forming at least one cutting edge in the monocrystalline silicon body by forming an etch mask over each body surface, with the etch mask formed over at least one of the body surfaces having an elongate opening therethrough to expose a portion of the body surface wherein the cutting edge is to be formed; anisotropic etching the exposed portion of the body surface through the opening in the etch mask down to the opposite body surface; and removing each etch mask. Each cutting edge is aligned substantially along a {111} crystalline plane of silicon. This can be done by using an anisotropic wet etchant such as potassium hydroxide (KOH), tetramethyl ammonium hydroxide (TMAH) or ethylenediamine pyrocatechol (EDP).

Each cutting edge can also be hardened by depositing a coating of a hard material (e.g. silicon nitride, titanium nitride, tungsten or amorphous diamond) over at least a part of the cutting edge. This coating can be deposited by a conventional vapor deposition process. Alternatively, a conformal coating of parylene can be deposited over at least a portion of each cutting blade.

Finally, a handle can be attached to the monocrystalline silicon body to hold the monocrystalline silicon body and each cutting edge in tension. Such a handle can be, for example, U-shaped.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1A:
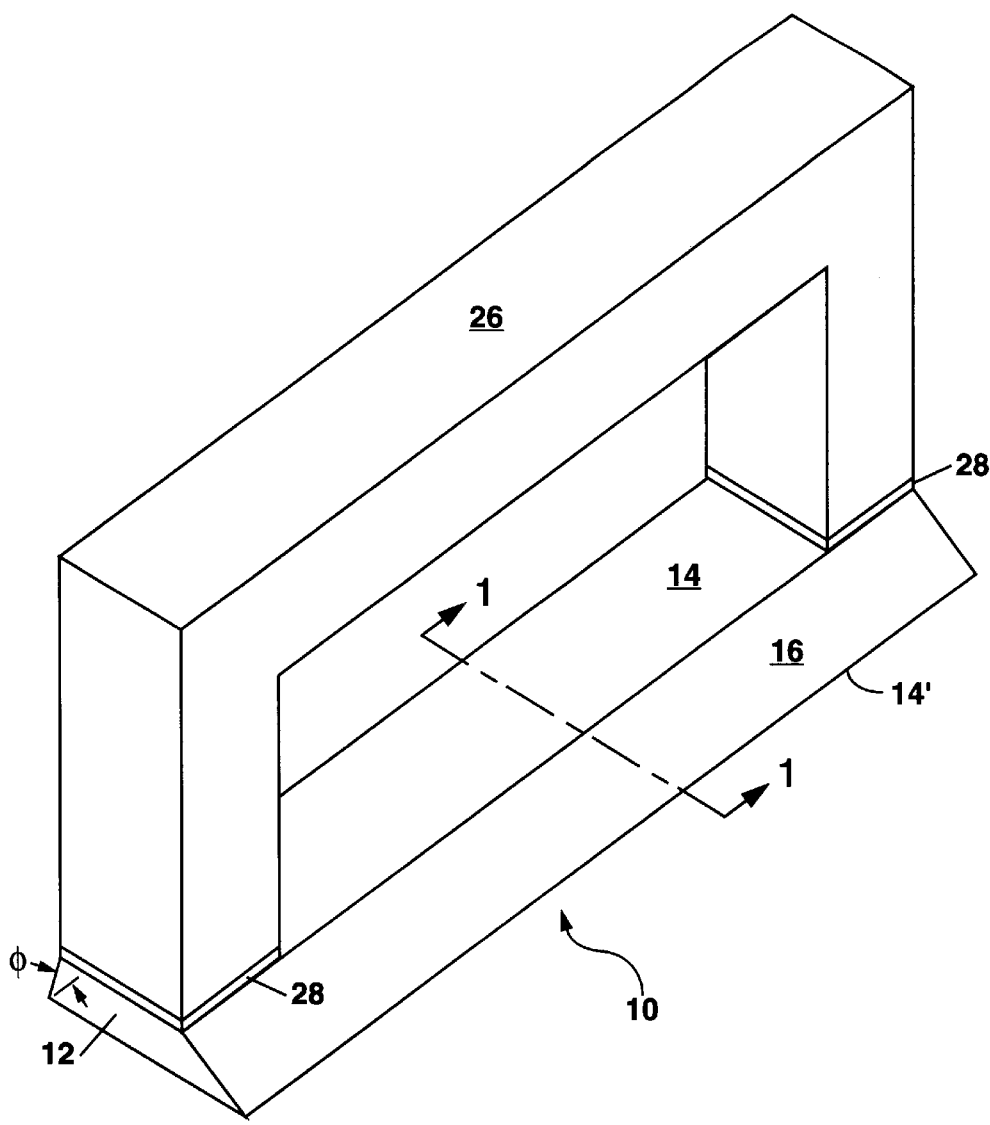
FIG. 1A shows a schematic perspective view of a micromachined cutting blade formed according to the present invention and mounted on a U-shaped handle.

Referring to FIG. 1A, there is shown schematically a first example of a micromachined cutting blade 10 formed according to the present invention, with the blade 10 being mounted in tension on a U-shaped handle 26. This example of the cutting blade 10 is single-edged and comprises an elongate body 12 (also termed herein a substrate) of monocrystalline silicon having a pair of substantially parallel major body surfaces 14 and 14' and a substantially planar cutting edge 16 formed at an acute angle θ to one of the major body surfaces (i.e. surface 14' in FIG. 1A) and oriented along the length of the body 12. The angle θ is generally less than 30° and preferably less than 20°.

In FIG. 1A, the monocrystalline silicon body 12, which can be part of a lightly-doped (e.g. $<5 \times 10^{19}$ cm$^{-3}$) monocrystalline silicon substrate (also referred to as a wafer), has major body surfaces 14 and 14' oriented substantially coplanar with a {211} crystalline plane of silicon (i.e. the surfaces 14 and 14' are formed substantially parallel to the {211} crystalline plane during fabrication of the substrate 12 wherefrom the cutting blade 10 is formed). This orientation is advantageous for producing a shallow angle θ for the cutting edge 16 using anisotropic wet etching as will be described in detail hereinafter. The shallow-angle cutting edge 16 is shown in detail in a cross-section view of the cutting blade 10 in FIG. 1B.

Figure 1B:
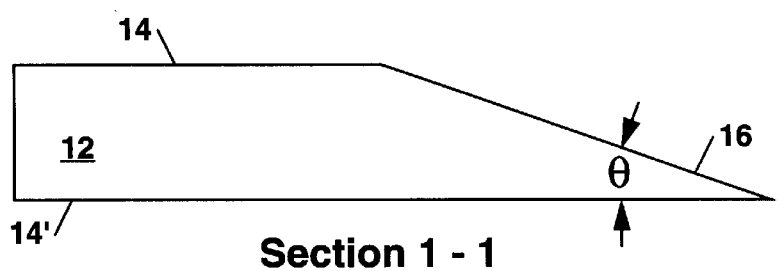
FIG. 1B shows a schematic cross-section view of the micromachined cutting blade along the section line 1—1 in FIG. 1A.

Fabrication of the single-edged cutting blade 10 in the example of FIGS. 1A and 1B will now be described with reference to FIGS. 2A–2E which describe a series of silicon micromachining process steps. Those skilled in the art will understand that generally rectangular cutting blades 10 of arbitrary dimensions can be fabricated using the silicon micromachining process described hereinafter. Furthermore, although fabrication of a single cutting blade 10 will be described, those skilled in the art will understand that the teachings of the present invention can be used to batch fabricate a plurality of cutting blades 10 of the same or different sizes on a common silicon substrate having a diameter of, for example, 4–8 inches. The individual blades 10 can then be separated either as a result of the anisotropic etching process (e.g. by anisotropically etching a plurality of sides of the blade 10 during formation of the cutting edge 16), or by sawing, cleaving, laser cutting etc. of one or more unetched sides of the blades 10. It should be noted that anisotropic etching of the two sides of the blade 10 adjacent to the cutting edge 16 results in the etching process being terminated upon reaching {111} crystalline planes of silicon that are oriented at an angle φ=61.9° degrees as measured from the major body surface 14' (see FIG. 1A). Furthermore, anisotropic etching of a side of the blade 10 opposite the cutting edge 16 results in the etching process being terminated at a {111} crystalline plane that is oriented 90° with respect the major body surfaces 14 and 14' (see FIG. 2B wherein this type of {111} plane is labelled "22").

Figure 2A:
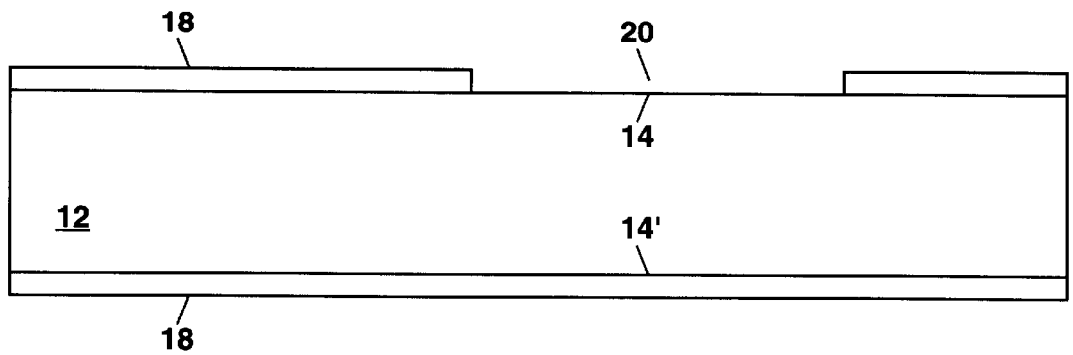
FIGS. 2A–2E show a series of processing steps for forming a first example of the present invention in the form of a single-edged cutting blade.

In FIG. 2A, a {211}-oriented monocrystalline silicon substrate 12 is provided for use in forming the cutting blade 10. The major body surfaces 14 and 14' of the substrate 12 are blanketed with an etch mask 18, with the etch mask 18 having an elongate (e.g. rectangular or U-shaped) opening 20 therethrough at a location wherein the cutting edge 16 is to be formed. The etch mask 18 can comprise, for example, about 500 nanometers of a silicate glass deposited by chemical vapor deposition (CVD) from the decomposition of tetraethylortho silicate (also termed herein as TEOS) and densified by heating to a high temperature for a specified period of time. The exact thickness of the etch mask 18 will depend upon the thickness of the substrate 12 being etched, and upon the particular anisotropic wet etchant being used.

After blanketing both surfaces 14 and 14' of the substrate 12 with the etch mask 18, the opening 20 in FIG. 2A can be formed by spinning a layer of photoresist (not shown) over the etch mask 18 on a top side of the substrate 12 and photolithographically defining a photoresist mask having a shaped opening identical to that of the opening 20 to be formed through the etch mask 18. Reactive ion etching can then be used to locally remove the TEOS glass to form the opening 20 as shown in FIG. 2A with the patterned photoresist layer protecting the remainder of the TEOS glass from being etched. After formation of the opening 20, the photoresist layer can be removed, leaving the patterned etch mask 18 in place. If needed, this process can be repeated to form a second opening 20 in the etch mask 18 covering the major body surface 14' (e.g. to form a double-edged cutting blade 10 as shown in FIGS. 3A–3E).

Figure 2B:
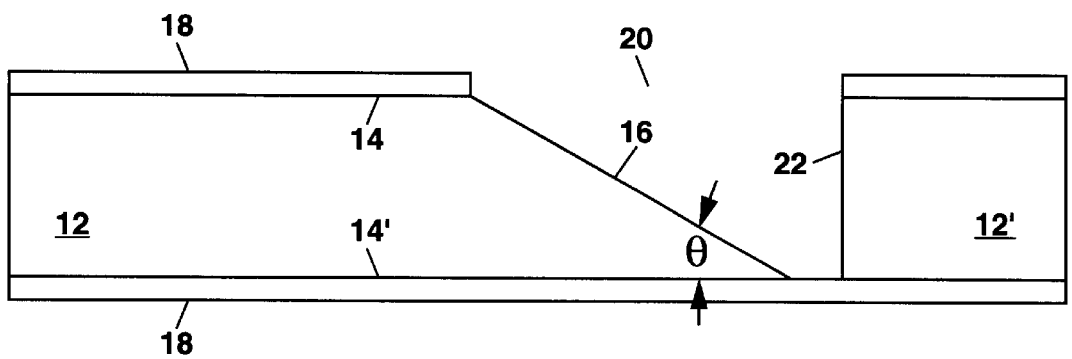

In FIG. 2B, the patterned etch mask 18 is used to selectively remove the underlying silicon material from the substrate 12 using an anisotropic wet etchant such as potassium hydroxide (KOH), tetramethyl ammonium hydroxide (TMAH) or ethylenediamine pyrocatechol (EDP). The anisotropic wet etchant selectively etches away the silicon substrate material over time without substantially attacking the etch mask 18. The anisotropic nature of the etching process results in the etching slowing down considerably upon reaching {111} crystalline planes of silicon so that the etching can be considered as being substantially terminated upon reaching the {111} planes. Meanwhile, the etching continues in other directions until other {111} crystalline planes are reached. As a result, after being etched for up to a few hours the substrate assumes the shape shown in FIG. 2B with a first {111} crystalline plane forming the substantially planar cutting edge 16 oriented at the angle θ=19.5° with respect to the major body surface 14', and with a second {111} crystalline plane 22 being oriented at an angle of 90° with respect to the same surface 14'. The opening 20 in the etch mask 18 is preferably made sufficiently wide so that the anisotropic etching extends completely through the thickness of the substrate to delineate a first substrate portion 12 which is used to form the cutting blade 10, and a second substrate portion 12' which can later be discarded once fabrication of the cutting blade 10 is completed.

Figure 2C:
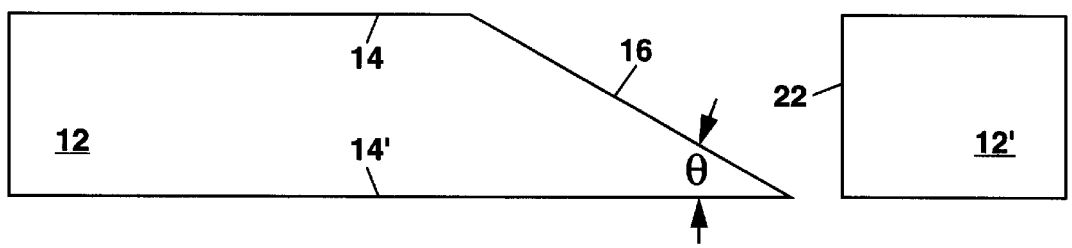

In FIG. 2C, the etch mask 18 is removed (i.e. stripped) from the substrate leaving the substrate portions 12 and 12' which are connected together at locations outside the elongate opening 20. Stripping of the etch mask 18 can be performed, for example, by etching with a selective wet etchant comprising hydrofluoric acid (HF). The HF-based etchant selectively etches the TEOS or other silicate glass forming the etch mask 18 while not substantially attacking silicon.

Figure 2D:
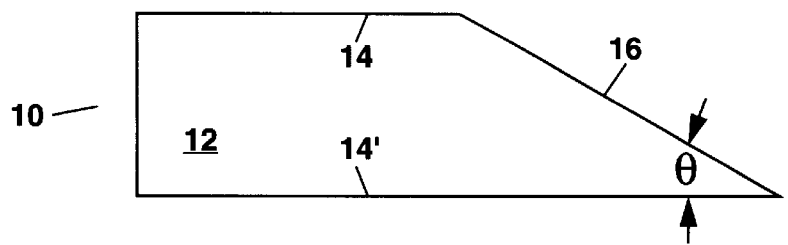

In FIG. 2D, the cutting blade 10 can be separated from the substrate portion 12' and any remaining substrate material using a conventional dicing technique such as saw cutting, laser cutting, or cleaving. In some instances, all sides of the blade 10 can be anisotropically etched so that the etching process separates the blade 10 from any remaining substrate material. The blade 10 can then be mounted onto an appropriate handle 26 for use.

For use in the LASIK procedure as described previously, the cutting blade 10 can be formed with a length that is generally in the range of 5–20 millimeters, a width of generally 1–5 millimeters, and a substrate thickness of generally 0.05–1 millimeter. For other applications, the cutting blade 10 can be formed with different lateral dimensions and thickness. For use in the LASIK procedure, the cutting blade 10 is preferably held in tension at its ends so that the blade can be used to make substantially planar cuts when the blade is reciprocated back and forth along its major axis and/or urged forward in a direction perpendicular to the major axis.

To hold the cutting blade 10 in tension, a generally U-shaped handle 26 can be used as shown in FIG. 1A, with the blade 10 being attached to the handle 26 at both ends under tension. The form of attachment, which will depend upon a particular design and material for the handle 26, can be, for example, solder 28 as shown in FIG. 1A, or alternately an adhesive (e.g. epoxy), screws or a pair of mechanical clamps at each end of the handle 26.

The blade 10 can be mounted on the handle 26 under tension, for example, by heating the blade 10 and the handle 26 when soldering the blade 10 the handle 26. By selecting the material (e.g. a metal or metal alloy, glass or fused silica) for the handle 26 to have a different coefficient of thermal expansion than that of the silicon blade 10, the blade 10 can be drawn into tension upon cooling of the handle 26 and blade 10 down to room temperature after the blade 10 is soldered to the handle 26.

As another example, when the blade 10 is attached to the handle 26 using an adhesive, screws or mechanical clamps, the handle 26 can be laterally compressed (e.g. in a vise) to reduce its length during the time when the blade 10 is being attached to the handle 26. Once the attachment is complete, the handle 26 can be restored to its former condition (e.g. by being removed from the vise) whereupon its length is increased to draw the blade 10 into a state of tension. Those skilled in the art will understand that other methods are available to attach the cutting blade 10 permanently or detachably to the handle 26. Furthermore, those skilled in the art will understand that other shapes can be provided for the handle 26, depending upon particular uses for the cutting blade 10.

To aid in aligning the blade 10 to the handle 26 and/or to properly tension the blade 10, optional alignment holes (not shown) can be etched or drilled through the blade 10 at either end for mating to pins (not shown) protruding from the ends of the handle 26.

Figure 2E:
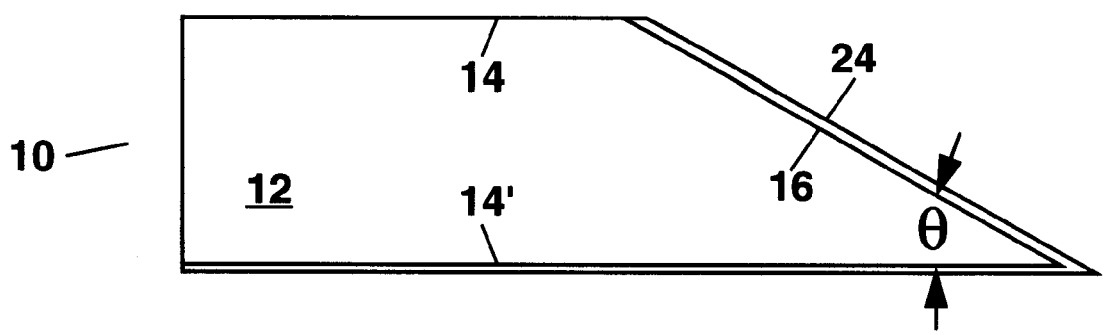

In FIG. 2E an optional coating 24 can be formed over the cutting edge 16 and/or one or more edge-adjoining surfaces (i.e. the major body surfaces 14 and 14'). The coating 24 can be formed at the stage of completion of the blade 10 shown in FIG. 2C (i.e. after removal of the etch mask 18 but while the blade 10 is still attached to substrate portion 12' along with other blades 10 formed on the same substrate). Alternately, the coating 24 can be formed on the cutting blade 10 after removal of the substrate portion 12' as shown in FIG. 2D. The coating 24 can either comprise a hard material for improving the strength and durability of the cutting edge 16 and edge-adjoining surfaces 14 and 14', or can comprise a conformal coating of parylene to reduce friction and improve biocompatibility of the cutting blade 10. Here, it should be noted that silicon is a biocompatible material so that no additional coating need be applied for surgical use.

The hard material can be, for example, silicon nitride, titanium nitride, or amorphous diamond deposited by a CVD process. Alternately, the hard material can be tungsten formed by a chemical reaction of a tungsten-containing gas such as tungsten hexafluoride ($WF_6$) with the silicon substrate material.

CVD deposition of silicon nitride and titanium nitride coatings are widely used in the semiconductor industry and are well-known to those skilled in the art so that they need not be described in great detail herein. Such silicon nitride or titanium nitride coatings 24 can be deposited by conventional low-pressure chemical vapor deposition (LPCVD) to a layer thickness of, for example, 0.1 to 10 $\mu$m. A low-stress silicon nitride coating 24 can be deposited, for example, by LPCVD at a temperature of 850° C. The deposition of titanium nitride can take place by LPCVD at about the same temperature.

Amorphous diamond can also be used to provide a hard coating 24 over the cutting edge 16 and/or the edge-adjoining surfaces 14 and 14'. Many different types of amorphous diamond coatings are known in the art, with each type of amorphous diamond comprising carbon atoms in a particular bonding arrangement. One type of amorphous diamond that is particularly well-suited for use forming the hard coating 24 is a low-stress amorphous tetrahedrally-coordinated carbon form (also termed herein as "a-tC") which contains a high percentage (generally $\geq$70%) of diamond-like bonds (i.e. 4-fold coordinated carbon atoms with $sp^1$ hybrid bonding), and with the remainder of the bonds therein being graphite-like bonds (i.e. 3-fold coordinated carbon atoms with $sp^2$ hybrid bonding). This a-tC coating 24 is transparent, insulating, smooth, extremely hard and contains negligible amounts (<0.1%) of hydrogen.

The a-tC coating 24 can be formed on the cutting edge 16 or edge-adjoining surfaces 14 and 14' by using pulsed laser deposition (PLD) with a rotating graphite target at room temperature which is irradiated by a krypton fluoride (KrF) laser operating at a wavelength of 248 nanometers and at a high laser fluence of >50 Joules-cm$^{-2}$. Prior to deposition, the cutting blade 10 can be immersed briefly into a dilute HF solution for up to a few minutes to provide a clean surface upon which the a-tC coating 24 can be deposited. The a-tC coating 24 can then be deposited using PLD to a coating thickness of, for example, 150–200 nanometers.

After deposition, the a-tC coating 24 is thermally annealed to reduce the stress therein as a result of the deposition process. This annealing step does not substantially affect the diamond-like properties of the a-tC coating 24, including its hardness. The annealing step can be performed, for example, by using a rapid thermal annealer (RTA) to quickly bring the cutting blade 10 with the deposited a-tC coating 24 up to an annealing temperature of about 600° C. in an inert gas (e.g. argon) ambient, with the cutting blade 10 being held at this temperature for a time period from a few minutes up to about one hour. The a-tC-coated cutting blade 10 can then be rapidly cooled back to room temperature after annealing. Thicker a-tC coatings 24 (e.g. up to 1–3 $\mu$m thick) can be formed by using a series of repeated deposition and annealing steps as described above to build the coating 24 up to a predetermined layer thickness. Further details of the a-tC coating process are disclosed in an article by J. P. Sullivan et al, "Stress Relaxation and Thermal Evolution of Film Properties in Amorphous Carbon," *Journal of Electronic Materials*, vol.26, pp. 1021–1029, 1997, which is incorporated herein by reference.

The formation of a tungsten coating 24 over the monocrystalline silicon cutting blade 10 can be performed as described hereinafter. The blade 10 is initially cleaned to remove any organic material. This can be done by exposing the silicon surfaces to an oxidizing ambient (e.g. an oxygen plasma, or a solution comprising hydrogen peroxide such as 5:1 $H_2SO_4:H_2O_2$ at a temperature of 95° C.) for up to about 10 minutes. Any oxide film (e.g. a native oxide film of silicon dioxide) on the surfaces of the blade 10 to be coated with tungsten is then removed by exposing the surfaces to a dilute HF solution for up to about 10 minutes. Immediately after the oxide cleaning step, the cutting blade 10 can be loaded into a vacuum chamber (e.g. an evacuated sample chamber of an LPCVD system) wherein a subsequent in situ $NF_3$ cleaning step is performed to remove any residual native oxide film. This $NF_3$ cleaning step can be performed by heating the blade 10 to about 45° C. and exposing the silicon surfaces to be coated with tungsten to gaseous $NF_3$ for up to 10 minutes. Deposition of the tungsten coating 24 can then take place in the same LPCVD system at the same elevated temperature by exposing the silicon surfaces to gaseous $WF_6$ at an overall pressure of about 400 milliTorr, for a time period of up to several minutes. The $WF_6$ reacts with any exposed silicon surfaces on the blade 10 to produce metallic tungsten (W) which is conformally deposited over the exposed silicon surfaces. The deposition of the tungsten coating 24 is self-limiting in that the deposition ceases once all the exposed silicon surfaces of the cutting blade 10 have been coated with metallic tungsten to a thickness of about 5–50 nanometers, since the silicon surfaces are coated and therefore are no longer accessible to the $WF_6$.

In other cases for reasons of biocompatibility or reduced friction, a conformal coating 24 of parylene can be formed over at least a portion of the cutting blade 10. This can be done either before or after attachment of the blade 10 to a handle 26, with the handle 26 in the latter case also being coated with parylene to form an integral coated assembly.

Parylene is a transparent conformal biocompatible coating that can be produced by the condensation and polymerization of a gaseous monomer, paraxylylene, at room temperature using vapor deposition polymerization (VDP) in a vacuum chamber. Parylene is available in three dimer forms designated as Parylene N (also termed di-para-xylylene or DPX-N), Parylene C (also termed dichloro-di-paraxylylene or DPX-C) and Parylene D (also termed tetra-chloro-di-para-xylylene or DPX-D). Parylene can be vapor deposited over the cutting blade 10 to form a coating 24 having a thickness in the range of 0.1 to 10$\mu$m or more. Furthermore, the parylene coating 24 can act as a dry-film lubricant to reduce friction and improve wear resistance of the cutting edge of the blade 10.

The VDP process takes place in a vacuum environment of 20–70 milliTorr and will be described hereinafter with reference to the formation of a Parylene N coating 24. A similar process is used to coat the cutting blade 10 with Parylene C or Parylene D; and this can be done with a commercially-available parylene deposition system.

Using the Gorham process as disclosed in U.S. Pat. No. 3,342,754, which is incorporated herein by reference, a parylene dimer, di-para-xylylene, is heated to about 150° C. resulting in its conversion to a gaseous dimer. This causes the gas pressure in the vaporization zone to rise, forcing the dimeric gas downstream into a pyrolysis zone where it is then heated to about 650° C., splitting the dimer molecules into highly reactive monomer molecules of para-xylylene. The monomer molecules continue to respond to pressure, flowing into the deposition chamber where they disperse and grow as a clear linear-polymer film on all surfaces to which the gas is exposed. The thickness of the resultant Parylene N coating 24 is controlled by the volume of the parylene dimer that is vaporized and by the dwell time in the deposition chamber. Since the parylene deposition process is gaseous, the coating thickness is uniform and conformal without any associated cure stress. The use of parylene coatings on surgical instruments is disclosed, for example, in U.S. Pat. No. 5,380,320 which is incorporated herein by reference.

In depositing the various coatings 24 described above masking techniques as known to the semiconductor processing art can be used to prevent the deposition of the coating 24 on particular surfaces of the cutting blade 10 (e.g. on a portion of surface 14 wherein the handle 26 is to be attached as shown in FIG. 1A), or to aid in removing the coating from particular surfaces after deposition.

FIGS. 3A–3E show a process for fabricating a second example of the cutting blade of the present invention in the form of a double-edged blade 30. Fabrication of the double-edged cutting blade 30 is similar to that described previously with reference to FIGS. 2A–2E except that openings 20 and 20' are formed in the etch mask 18 on both surfaces 14 and 14' of the {211}-oriented monocrystalline silicon substrate 12, with the openings 20 and 20' being laterally offset with respect to each other and located wherein each cutting edge 16 and 16' of the blade 30 is to be formed. The exact locations and shapes of the openings 20 and 20' will depend upon predetermined dimensions for the cutting blade 30 and on how many edges of the blade 30 are to be formed by etching (e.g. whether just the two cutting edges 16 and 16' are to be formed by etching or whether the remaining sides of the blade 30 are also to be formed by etching).

Figure 3A:
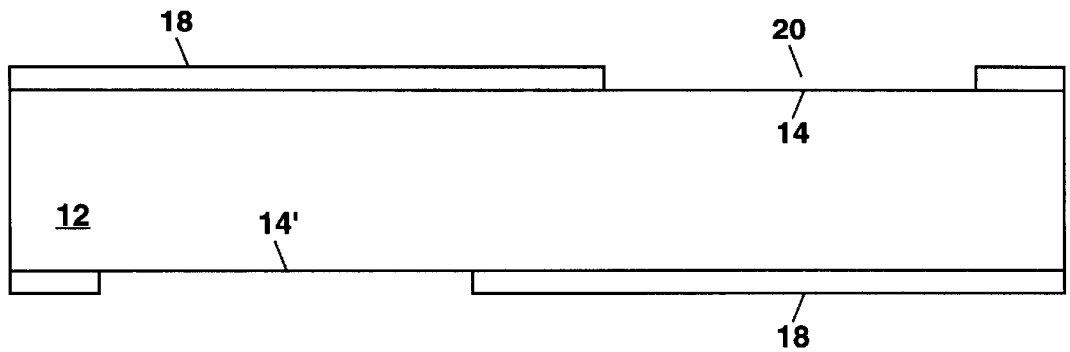
FIGS. 3A–3E show a series of processing steps for forming a second example of the present invention in the form of a double-edged cutting blade.

In FIG. 3A, the etch mask 18 is formed over the major body surfaces 14 and 14' as described with reference to FIG. 2A. Elongate (e.g. rectangular or U-shaped) openings 20 are then formed through the etch mask 18 at the location of each cutting edge 16 to be formed.

Figure 3B:
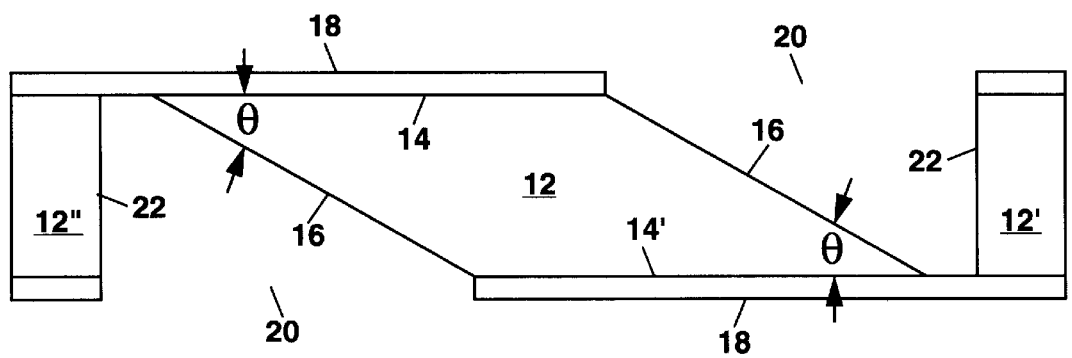

In FIG. 3B, both major body surfaces 14 and 14' of the substrate 12 are anisotropically etched through the openings 20 and 20' to form the two cutting edges 16 and 16'. The etching step can proceed as described previously with reference to FIG. 2B. As the etching takes place simultaneously on both surfaces 14 and 14' of the substrate 12, the cutting edges 16 and 16' are formed when the anisotropic wet etching process substantially terminates upon reaching a pair of parallel {111} crystalline planes of silicon. This results in each cutting edge 16 and 16' being oriented at the same angle $\theta = 19.5°$ with respect to one of the {211}-oriented major body surfaces 14 or 14' as shown in FIG. 3B. As a result of the etching, the original substrate in FIG. 3A is divided into three portions, with a first substrate portion that forms the cutting blade 30 being designated as substrate portion 12 in FIG. 3B, and with the remainder of the original substrate of FIG. 3A being designated as substrate portions 12' and 12" in FIG. 3B. The substrate portions 12' and 12" can be discarded once fabrication of the blade 30 is completed.

Figure 3C:
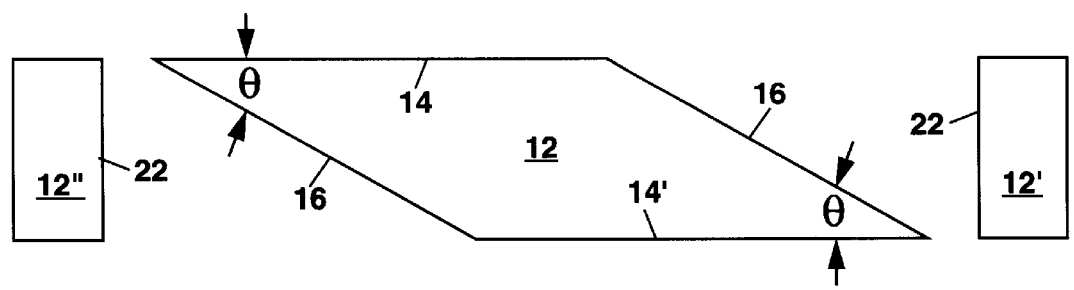

In FIG. 3C, the etch mask 18 is removed from the substrate as described previously with reference to FIG. 2C. This leaves the substrate portions 12, 12' and 12" connected together at locations outside the elongate openings 20 and 20' when these openings in the etch mask 18 are rectangular. If each opening 20 and 20' were U-shaped (e.g. with a forked side of one U-shaped opening 20 being oriented to face the forked side of the other U-shaped opening 20') to allow the remaining sides of the cutting blade 30 to be etched at the same time the cutting edges 16 and 16' are formed, then the individual blade(s) 30 can be released from the original substrate upon completion of the etching step since the substrate portions 12' and 12" would no longer be connected to the substrate portion 12 forming the completed blade 30.

Figure 3D:
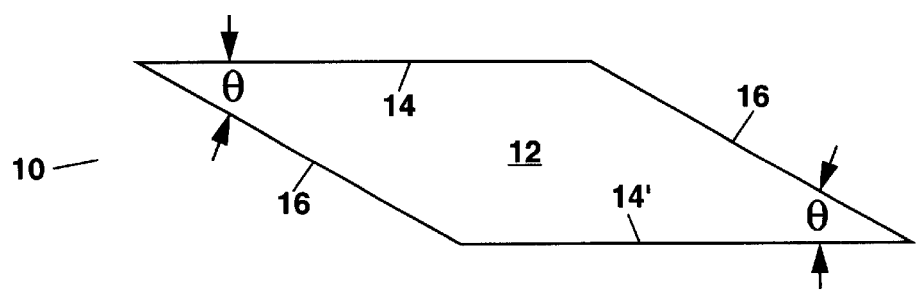

In FIG. 3D, if necessary the substrate portions 12' and 12" can be removed using a conventional dicing technique as described previously with reference to FIG. 2D. The resultant double-edged cutting blade 30 can then be mounted onto an appropriate handle 26 for use as described with reference to FIG. 1A. The various dimensions for the double-edged cutting blade 30 can be, for example, in the same range as the dimensions previously recited for the single-edged cutting blade 10 of FIGS. 1A and 1B, with the exact dimensions depending upon a particular use for the double-edged cutting blade 30.

Figure 3E:
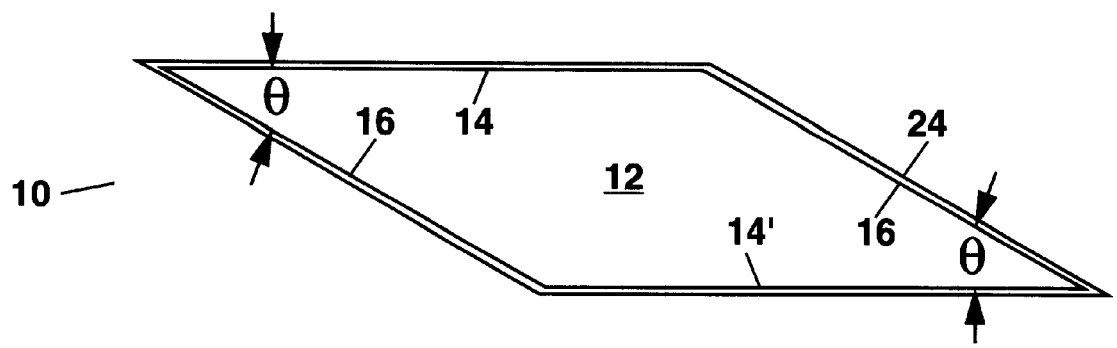

In FIG. 3E, the double-edged cutting blade 30 can be optionally coated as described previously with reference to FIG. 2E, with the coating 24 comprising, for example, silicon nitride, titanium nitride, tungsten, amorphous diamond or parylene. The coating 24 can cover all of the blade 30 as shown in FIG. 3E; or alternately the coating 24 can cover only a part of the blade 30 (e.g. the cutting edges 16 and 16', and/or the one or more of the edge-adjoining surfaces 14 and 14'). The coating 24 can be formed either before or after removal of the cutting blade 30 from the substrate portions 12' and 12". In some instances (e.g. for parylene), the coating 24 can be applied after mounting the blade 30 to a handle 26 with the coating 24 covering both the blade 30 and handle 26.

The matter set forth in the foregoing description and accompanying drawings is offered by way of illustration only and not as a limitation. Other applications and variations of the apparatus and method of the present invention will become evident to those skilled in the art. Those skilled in the art will understand that other shapes for the opening(s) 20 and 20' in the etch mask 18 are possible so that a plurality of sides of the cutting blades 10 and 30 can be simultaneously etched to terminate upon reaching {111} crystalline planes of silicon, with the individual {111} planes being oriented as described previously with reference to FIGS. 1A and 2B. Furthermore, those skilled in the art will understand that other shapes can be used for the handle 26 than that shown schematically in FIG. 1A, with the shape of a particular handle 26 being selected for a particular application of the cutting blades 10 and 30. Finally, those skilled in the art will understand that the cutting blades 10 and 30 of the present invention have uses other than for surgery. For example, the cutting blades 10 and 30 can be used for shaving, or in a microtome. The actual scope of the invention is intended to be defined in the following claims when viewed in their proper perspective based on the prior art.

What is claimed is:

1. A micromachined cutting blade, comprising:
   (a) an elongate body of monocrystalline silicon having a pair of substantially parallel major body surfaces, with each major body surface being aligned substantially coplanar with a {211} crystalline plane of silicon; and
   (b) a substantially planar cutting edge formed in the monocrystalline silicon body at an acute angle to one of the major body surfaces and oriented along the length of the body by intersection of a {111} crystalline plane of silicon with the {211} crystalline plane.

2. The blade of claim 1 wherein the angle is 19.5 degrees.

3. The blade of claim 1 further including a coating of a hard material covering at least a part of the cutting edge.

4. The blade of claim 3 wherein the coating comprises silicon nitride.

5. The blade of claim 3 wherein the coating comprises titanium nitride.

6. The blade of claim 3 wherein the coating comprises tungsten.

7. The blade of claim 3 wherein the coating comprises amorphous diamond.

8. The blade of claim 1 further including a conformal coating of parylene covering at least a portion of the cutting blade.

9. The blade of claim 1 further including a handle connected to opposite ends of the elongate body to support the elongate body in tension.

10. The blade of claim 9 wherein the handle is U-shaped.

* * * * *